United States Patent [19]

Ochoa Gomez et al.

[11] Patent Number: 5,225,592
[45] Date of Patent: Jul. 6, 1993

[54] PROCEDURE FOR OBTAINING DERIVATIVES FROM ACETIC ACID

[75] Inventors: Jose Ochoa Gomez; Juan Martin Ramon; Jose Sanchez Sanchez; Asuncion De Diego Zori, all of Madrid, Spain

[73] Assignee: Ercros S.A.

[21] Appl. No.: 859,357

[22] PCT Filed: Sep. 24, 1991

[86] PCT No.: PCT/ES91/00060
§ 371 Date: Jun. 12, 1992
§ 102(e) Date: Jun. 12, 1992

[87] PCT Pub. No.: WO92/05144
PCT Pub. Date: Apr. 2, 1992

[30] Foreign Application Priority Data

Sep. 25, 1990 [ES] Spain ................................. 9002448

[51] Int. Cl.$^5$ ............................................. C07C 51/16
[52] U.S. Cl. ........................................................ 562/526
[58] Field of Search ........................................... 562/526

[56] References Cited

U.S. PATENT DOCUMENTS 3,842,081 10/1974 Schulze et al. ................. 260/268 R
4,319,037 3/1982 Yoneoka ............................. 560/239
4,782,183 11/1988 Goto et al. ......................... 562/526

FOREIGN PATENT DOCUMENTS 2103724 8/1972 Fed. Rep. of Germany.
1440754 6/1976 United Kingdom.
2148287 5/1985 United Kingdom.

*Primary Examiner*—Arthur C. Prescott
*Attorney, Agent, or Firm*—Frank D. Shearin

[57] ABSTRACT

Procedure for obtaining acetic acid derivatives (I) where $R_1$ and $R_2$ are H or groups —$CH_2$—COOH by oxidation of (II) where R and R' are H or groups of —$CH_2$—$CH_2OH$ with $O_2$ or a gas that contains it, in the presence of an metal hydroxide, demineralized water and Cu-Raney. The reaction is carried out keeping constant a partial pressure of oxygen below 20 $Kg/cm^2$, inside the reactor. The acids (I) obtained as soluble salts, can be isolated and purified by chemical or electrochemical means.

Examples of acids (I) are glycine, iminediacetic acid and nitricetriacetic acid, useful as nutrients and in the synthesis of herbicides.

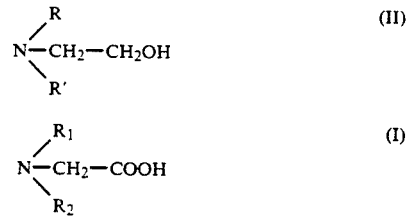

10 Claims, No Drawings

PROCEDURE FOR OBTAINING DERIVATIVES FROM ACETIC ACID

FIELD OF THE INVENTION

The invention concerns a procedure for obtaining derivatives of acetic acid, specifically glycine and iminodiacetic and nitrilotriacetic acids by oxidizing monoethanolamine, diethanolamine and triethanolamine, respectively, with the use of oxygen or a gas that contains oxgygen and a Copper-Raney catalyst.

BACKGROUND TO THE INVENTION

The glycine, the iminodiacetic acid (I.D.A.) and the nitrilotriacetic acid (N.T.A.), described in numerous patents, are widely used in different sectors. For example, glycine can be used as a nutrient and both I.D.A. and N.T.A. are used in the process of synthesizing herbicides, among other applications. Since these products have appeared on the market, a variety of ways of obtaining them have been described and patented.

The Japanese patent 53/7709 held by the Mitsui Toatsu Chemical Co. Ltd, describes a procedure for obtaining I.D.A. and N.T.A. through the oxidation of diethanolamine and triethanolamine respectively, with oxygen gas in a base aqueous solution, using a noble metal (Pt and Pd) as catalyst for the reaction. Although the acids mentioned can be obtained through this procedure, the yield obtained for both I.D.A. (69%) and N.T.A. (60%), is rather low, and there is the added drawback that the possible losses of the noble metal used as a catalyst make this process unprofitable from an economic point of view. On the other hand, it is a fact, recognised by experts in catalysis, that noble metal losses occur in catalytic processes both for acids and bases, through the solution of the metal in the reaction water, a complex process being required for their recovery, and that there are also losses when the above-mentioned catalysts are being handled. As a result, it is difficult to make this type of process profitable considering that the end-products are of little economic value.

So, it would be useful if a process existed through which glycine and the acids I.D.A. and N.T.A. could be obtained in such a state of purity and with sufficiently high yields resulting from oxidation of mono-, di- and triethanolamine, respectively, using a catalyst that was not a noble metal (e.g. Copper-Raney), that the aforementioned economic shortcomings would be reduced to a minimum.

Therefore, one of the aims of the invention is to provide a procedure for oxidizing mono-, di- and triethanolamine, in the presence of a Copper-Raney catalyst, which gives good yields in the reaction performance as well as minimizing cost of the catalyst when obtaining the end-product.

On the other hand, other Japanese patents held by Nippon Catalytic Chem. Ind., 60/78.948, 60/78.949, 60/97.945, 60/100.545 and 61/65.840, provide a procedure for obtaining glycine, I.D.A. and N.T.A. by oxidizing the mono-, di- and triethanolamine in a base aqueous solution using Copper-Raney as a catalyst, but with oxygen or gas that contains oxygen, obtained using a water decomposition reaction according to the following reaction diagrams, respectively:

In this procedure calculating, for example theoretically, the heat of the combustion and reaction required to obtain the iminodiacetic acid, this would be 2,053 Kcal/Kg of I.D.A. and the amount of hydrogen produced would be around 0.061 Kg $H_2$/Kg of I.D.A. So, for a load of 13.5 Kg of I.D.A. produced in 4 hours using the above-mentioned Japanese patent no. 69/78,948, the amount of hydrogen released would be 0.81 Kg that, at 25° C. and 1 atmosphere, would be equivalent to 41 liters of hydrogen per minute, and this would have to be allowed to leave the reaction so that it could be carried out at the pressure of 9 Kg/cm$^2$ which is referred to in the patent. So, in order to adopt this procedure, it would be necessary to have fireproof installations, and to work in greater safety conditions due to the presence of the hydrogen, and furthermore, the amount of heat to be delivered would have a considerable effect on the final manufacturing cost of the end-products.

As a result of the aforementioned, a second aim of this invention is to provide a mono-, di- and triethanolamine oxidation procedure in the presence of a Copper-Raney catalyst, this type being the same as in the two previous procedures, but with the advantage of it not being necessary to carry out the procedure in fireproof installations, plus the additional advantages of notably reducing the safety conditions for the procedure and reducing to a minimum the heat expenses required to manufacture the desired compounds.

The two aims of the procedure adopted for this invention arise from the new technology for the manufacture of glycine, I.D.A. and N.T.A., which are carried out according to the following reaction diagrams:

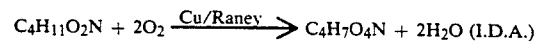

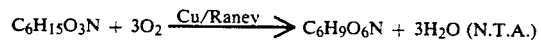

which are slightly exothermic reactions, without releasing hydrogen and carried out without the use of noble metals but with Copper-Raney as the catalyst.

BRIEF DESCRIPTION OF THE INVENTION

The invention deals with a procedure for obtaining acetic acid derivatives, specifically glycine, iminodiacetic acid and nitrilotriacetic acid by oxidation with $O_2$ or a gas which contains it, of mono-, di- and triethanoamine respectively, in reactions carried out with hardly any hydrogen and in the presence of a Copper-Raney catalyst. To bring about this reaction, it is suggested that the process should start without any sweeping taking place with nitrogen or hydrogen, once the components of the reaction have been added and the heating begun for the obtaining of the temperatures and pressures mentioned below. In addition, the catalyst to be used is Copper-Raney, wetted for safety reasons.

DETAILED DESCRIPTION OF THE INVENTION

The invention provides a procedure for obtaining the acetic acid derivatives of general formula (I)

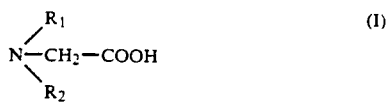

where $R_1$ and $R_2$ can either be H or $-CH_2-COOH$ groups independently.

The procedure for the invention can be represented by the following reaction diagram in which Copper-Raney FIGURES as the catalyst.

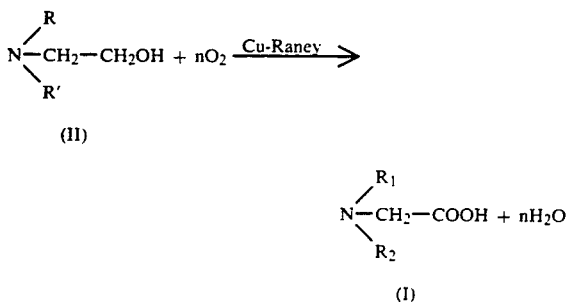

where R and R' can be H or $-CH_2-CH_2OH$ groups independently.

As can be seen, when $R=R'=H$, the aminoalcohol (II) is the monoethanolamine and compound (I) obtained is the glycine ($R_1=R_2=H$). Likewise, when one of either R or R' is H and the other is $-CH_2-CH_2OH$, compound (II) is the diethanolamine and the compound (I) obtained is the iminodiacetic acid (one of either $R_1$ or $R_2$ is H and the other is $-CH_2-COOH$), and when $R=R'=-CH_2-CH_2OH$, the compound (II) is triethanolamine and compound (I) obtained is nitrilotriacetic acid. The above reaction diagram n, can have the values 1, 2 or 3, respectively.

Thus the invention procedure includes the oxidation of an aminoalcohol in formula (II)

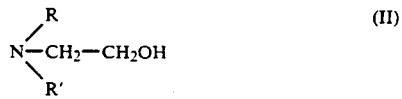

where R and R' can either be H or $-CH_2-CH_2OH$ groups independently with $O_2$ or with a gas that contains $O_2$.

The reaction can be carried out at temperatures ranging from 25° C. to 200° C., preferably between 150° C. and 195° C. It can take place at a partial $O_2$ pressure inside the reactor, at 20 $Kg/cm^2$, preferably between 2 and 13 $Kg/cm^2$. Water is used as a solvent, and an alkalimetal hydroxide in a molar relation with respect to the hydroxide groups of the initial aminoalcohol (II) has been added, situated between 5% and 20% in stoichiometric excess, preferably between 5% and 10%. This means that from 1.05 to 1.10 moles of alkalimetal hydroxide are used per mol of monoethanolamine, from 2.10 to 2.20 moles of the hydroxide per mol of diethanolamine and from 3.15 to 3.30 moles of alkalimetal hydroxide per mol of triethanolamine. An alkalimetal hydroxide can be used as long as the salts formed with the acids obtained are soluble in the reaction environment. It is preferable that these salts are soluble in water at a temperature of 80°-95° C. Sodium hydroxide and potassium hydroxide are examples of suitable Alkaline Hydroxides.

The initial concentration of the aminoalcohols (II) ranges between 20% and 35% in weight, with reference to the total initial weight of the components of the reaction mass, preferably between 30% and 35% in weight. Larger concentrations can cause yield losses as a result of diffusion of the oxidant gas, and lower concentrations reduce the productivity without improving the results. The catalyst used in the invention procedure is Copper-Raney, although it is also possible to use a Nickel-Raney catalyst if small modifications are made in the process. The Copper-Raney catalyst can be easily manufactured through leaching with sodium hydroxide in a reducing atmosphere of the alloy $Al_2Cu$, following the procedures that have already been mentioned. The catalyst is added in amounts less than the 30% weight of the initial aminoalcohol (II) content, preferably between 15% and 30% in weight, although with an average percentage of 25%, it is possible to obtain excellent results.

The oxidizing agent is oxygen or a gas containing oxygen such as air or synthetic air, no more than the minimum amount necessary being used to maintain the reaction of the above-mentioned partial pressure of $O_2$ (less than 20 $Kg/cm^2$), and no more than the gas necessary should be used as a replacement.

The time the reaction takes, operating in these conditions, ranges from 3.5 to 5.0 hours depending on the number of times the catalyst is used.

The reaction is monitored by measuring the conversion of the initial aminoalcohol (II) and the appearance of the acetic acid derivative (I). Once the reaction is completed, the reaction environment is subjected to a filtration process under heat, at a temperature of between 80° C. and 95° C., preferably between 85° C. and 90° C., with a view to recovering the catalyst used, so that it can be regenerated and reused in successive reaction cycles.

After this, the base solution in the reaction environment, that which contains the soluble alkaline salts from the derivatives of the acetic acid, is subjected to an isolation and purification process so that the corresponding acids from formula (I) can be obtained. This treatment can be carried out either by chemical means, through crystalization of the reaction solution at temperatures ranging from 75° C. to 85° C., preferably between 80° C. and 85° C., of the reaction solution after it has been treated with hydrochloric acid, so as to obtain a pH of between 0.5 and 2.5, depending on the acid obtained, or by electrochemical means, applying the electrodialysis procedure referred to in the Spanish patent no 9000130 (held by person who is applying for a patent for this invention).

The present invention can been clearly illustrated with the following examples, which should not be regarded as restrictive but simply serving as references, and which make it easier to understand the nature of the invention procedure.

EXAMPLE 1

183 g. of 97% sodium hydroxide; 300 g. of demineralized water; 163.2 g. of 98% diethanolamine; 64 g. of Copper-Raney with a humidity level of 30%, which really means using 44.8 g. of net-weight catalyst in the test, and finally 40 further g. of demineralized water, to break down all the previous reagents, are all stirred into a stainless steel autoclave reactor (AISI 316) with a 1 liter capacity, and in the above-mentioned order. Then, and while still stirring, the heating process is started until 170° C. is reached and the pressure inside the reactor is 18 Kg/cm². At this stage, the reactor is brought into contact with a shot of oxygen previously set at 18 Kg/cm² so as to have the same pressure and making sure that the pressure is kept constant during the course of the process, the oxygen consumed being continually replaced. The suspension is continuously stirred for 3.5 hours. When this time has elapsed, the reaction is concluded, and it is cooled to 90° C. and filtered with suction with Buchner and Kitasato, regaining the humidity weight of 71.0 g. of the copper catalyst, this being kept for successive reuse after regeneration. The reaction solution, once analyzed by chromotography, provides a 95% yield of free iminodiacetic acid in the form of disodium salt, and this can be easily isolated and purified either by crystalization at 85° C. at pH 22, or electrochemically using one of the electrodialysis processes mentioned before. The purification yield is quantitative (100%) using the isolation procedure and purification by electrodialysis.

EXAMPLE 2

An experiment carried out with the same methodology as in Example 1, but using 201.25 g. of 98.5% monoethanolamine; 144.3 g. of 97% sodium hydroxide; 338.15 g. of demineralized water and 66.2 g. of Copper-Raney with an approximate humidity of 25%, which amounts to 49.6 g. in net weight. The temperature of the reaction was 155° C. and the duration 4.25 hours. The final yield of the reaction was 85.8% glycine. The isolation and purification in this case, was carried out by electrodialysis and a substantial purification yield was obtained.

The aim of the present invention having been described, the following are stated as being essential to it.

We claim:

1. A process for preparing amino acid salts represented by the formula:

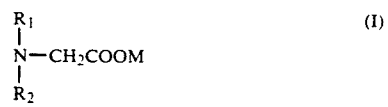

wherein $R_1$ and $R_2$ are independently selected from the group consisting of H and -CH$_2$COOM, and M is an alkali metal, which comprises bringing together under reaction conditions an aqueous solution of an aminoalcohol represented by the formula

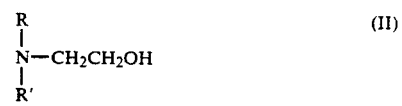

wherein R and R' are independently selected from the group consisting of H and CH$_2$CH$_2$OH, molecular oxygen or a gas containing molecular oxygen, an alkali metal hydroxide and in the presence of a Raney copper catalyst.

2. A process of claim 1 wherein the amount of Raney copper catalyst is between about 15 weight percent and about 30 weight percent, based on the weight of the initial aminoalcohol present.

3. A process of claim 1 wherein the alkali metal hydroxide is sodium hydroxide or potassium hydroxide.

4. A process of claim 1 wherein the temperature of the reaction is between 25° C. and about 200° C.

5. A process of claim 4 wherein the temperature is between about 150° C. and about 195° C.

6. A process of claim 1 wherein the partial pressure of oxygen is between about 2 and about 20 Kg/cm².

7. A process of claim 6 wherein the partial pressure of oxygen is between about 2 and about 13 Kg/cm².

8. A process of claim 3 wherein the aminoalcohol is monoethanolamine and the amino acid salt is the alkali metal salt of glycine.

9. A process of claim 3 wherein the aminoalcohol is diethanolamine and the amino acid salt is the di-alkali metal salt of iminodiacetic acid.

10. A process of claim 3 wherein the aminoalcohol is triethanolamine and the amino acid salt is the tri-alkali metal salt of nitrilotriacetic acid.

* * * * *